US012654157B2

(12) United States Patent
Sheehan et al.

(10) Patent No.: US 12,654,157 B2
(45) Date of Patent: Jun. 16, 2026

(54) MODIFIED COPPER-ZINC CATALYSTS AND METHODS FOR ALCOHOL PRODUCTION FROM CARBON DIOXIDE

(71) Applicant: Air Company Holdings, Inc., Brooklyn, NY (US)

(72) Inventors: Stafford W. Sheehan, Tiverton, RI (US); Chi Chen, Shrewsbury, MA (US)

(73) Assignee: Air Company Holdings, Inc., Brooklyn, NY (US)

( * ) Notice: Subject to any disclaimer, the term of this patent is extended or adjusted under 35 U.S.C. 154(b) by 669 days.

(21) Appl. No.: 18/003,236

(22) PCT Filed: Jun. 24, 2021

(86) PCT No.: PCT/US2021/038802
§ 371 (c)(1),
(2) Date: Dec. 23, 2022

(87) PCT Pub. No.: WO2021/262922
PCT Pub. Date: Dec. 30, 2021

(65) Prior Publication Data
US 2023/0256423 A1 Aug. 17, 2023

Related U.S. Application Data

(60) Provisional application No. 63/114,783, filed on Nov. 17, 2020, provisional application No. 63/044,175, filed on Jun. 25, 2020.

(51) Int. Cl.
B01J 23/80 (2006.01)
B01J 21/04 (2006.01)
(Continued)

(52) U.S. Cl.
CPC ............... B01J 23/80 (2013.01); B01J 21/04 (2013.01); B01J 21/185 (2013.01); (Continued)

(58) Field of Classification Search
CPC ....... C07C 29/159; C07C 31/04; C07C 31/08; B01J 23/80; B01J 21/04; B01J 23/8873
See application file for complete search history.

(56) References Cited

U.S. PATENT DOCUMENTS 4,659,742 A 4/1987 Courty et al.
4,791,141 A 12/1988 Chaumette et al.
(Continued)

FOREIGN PATENT DOCUMENTS

CN 102513113 A 6/2012
CN 102350359 B 3/2013
(Continued)

OTHER PUBLICATIONS

Ning et al (CN 103721719 machine translation), Apr. 16, 2014.*
(Continued)

*Primary Examiner* — Jafar F Parsa
(74) *Attorney, Agent, or Firm* — Foley Hoag LLP; Lucas P. Watkins; Lucas A. Freeman

(57) ABSTRACT

The present disclosure provides catalysts, comprising: copper; zinc; one or more first elements selected from iron, nickel, or cobalt; aluminum; oxygen; optionally, one or more second elements selected from a Group V, VI, VII, VIII, IX, X, and XI metal (e.g., manganese, silver, niobium, zirconium, molybdenum, ruthenium, or palladium); and optionally, one or more Group IA metals, and wherein the first element is present in an amount of about 1 to about 40 wt. % (e.g., about 1 to about 10 wt. %, about 25 to about 40 wt. %, about 30 to about 40 wt. %, or about 35 to about 40 wt. %) of the total amount of the copper, zinc, first element, the optional second element, and the optional Group IA metal, and methods of using said catalyst in the production of ethanol and higher alcohols from carbon dioxide.

12 Claims, 1 Drawing Sheet

(51) Int. Cl.

| | |
|---|---|
| *B01J 21/18* | (2006.01) |
| *B01J 23/847* | (2006.01) |
| *B01J 23/887* | (2006.01) |
| *B01J 23/889* | (2006.01) |
| *B01J 35/30* | (2024.01) |
| *B01J 35/45* | (2024.01) |
| *B01J 35/50* | (2024.01) |
| *B01J 35/61* | (2024.01) |
| *B01J 35/63* | (2024.01) |
| *B01J 37/00* | (2006.01) |
| *B01J 37/02* | (2006.01) |
| *B01J 37/03* | (2006.01) |
| *B01J 37/04* | (2006.01) |
| *B01J 37/08* | (2006.01) |
| *C07C 29/154* | (2006.01) |
| *C07C 29/156* | (2006.01) |

(52) U.S. Cl.

CPC ....... *B01J 23/8474* (2013.01); *B01J 23/8873* (2013.01); *B01J 23/8892* (2013.01); *B01J 35/393* (2024.01); *B01J 35/45* (2024.01); *B01J 35/613* (2024.01); *B01J 35/615* (2024.01); *B01J 35/617* (2024.01); *B01J 35/633* (2024.01); *B01J 35/635* (2024.01); *B01J 35/638* (2024.01); *B01J 37/0036* (2013.01); *B01J 37/0205* (2013.01); *B01J 37/0213* (2013.01); *B01J 37/0236* (2013.01); *B01J 37/035* (2013.01); *B01J 37/04* (2013.01); *B01J 37/088* (2013.01); *C07C 29/154* (2013.01); *C07C 29/156* (2013.01); *B01J 35/50* (2024.01)

(56) References Cited

U.S. PATENT DOCUMENTS

| | | | |
|---|---|---|---|
| 2011/0041517 A1* | 2/2011 | Takagi ................. | C21C 5/4673 |
| | | | 423/220 |
| 2014/0128642 A1 | 5/2014 | Weiner et al. | |
| 2016/0311740 A1 | 10/2016 | Liu et al. | |
| 2018/0361362 A1 | 12/2018 | Gordon et al. | |
| 2019/0262803 A1 | 8/2019 | Yu et al. | |
| 2020/0102866 A1 | 4/2020 | Ishikawa | |

FOREIGN PATENT DOCUMENTS

| | | |
|---|---|---|
| CN | 103084203 A | 5/2013 |
| CN | 106563455 A | 4/2017 |
| JP | 2704165 B2 | 1/1998 |
| WO | WO-01/000320 A1 | 1/2001 |
| WO | WO-2019/010095 A1 | 1/2019 |
| WO | WO-2021/262922 | 12/2021 |

OTHER PUBLICATIONS

Cai et al., comparison of the promoted CuZnMxOy catalyst for carbon dioxide hydrogenation to methanol, (Catalysis Letter (2019) 149 pp. 2508-2518).*

Extended European Search Report for EP Application No. 21828545.0 dated Jul. 8, 2024.

International Search Report and Written Opinion for International Application No. PCT/US21/38802 mailed Oct. 1, 2021.

\* cited by examiner

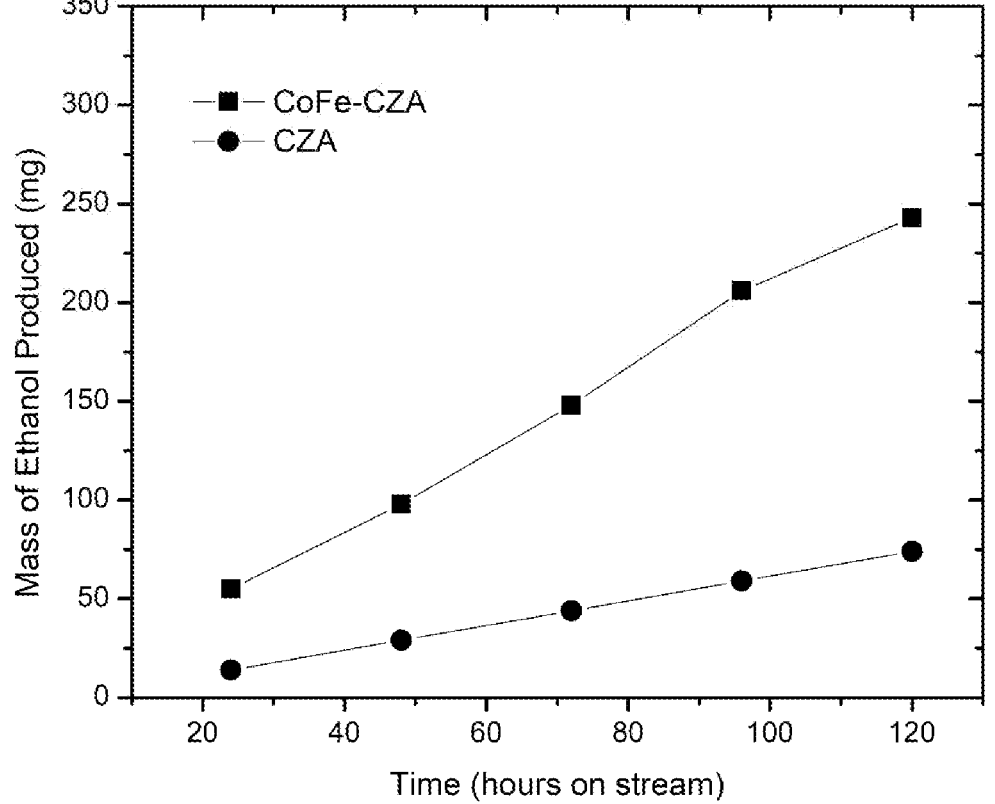

1

MODIFIED COPPER-ZINC CATALYSTS AND METHODS FOR ALCOHOL PRODUCTION FROM CARBON DIOXIDE

CROSS-REFERENCE TO RELATED APPLICATIONS

This application is a US National Phase entry under 35 USC § 371 of International Patent Application No. PCT/US2021/038802, filed Jun. 24, 2021; which claims the benefit of priority to U.S. Provisional Patent Application No. 63/044,175, filed Jun. 25, 2020; and U.S. Provisional Patent Application No. 63/114,783, filed Nov. 17, 2020. The entire contents of each of these applications is incorporated herein by reference.

FIELD OF THE INVENTION

The present invention relates to the field of heterogeneous catalysts, specifically for catalysts that convert hydrogen gas and carbon dioxide into other materials.

BACKGROUND OF THE INVENTION

As carbon dioxide concentrations in the atmosphere increase, it is becoming advantageous from social welfare, human health, and energy security perspectives to develop technologies that remove carbon dioxide from the air. Carbon dioxide conversion technologies have the added benefit of producing commodity chemicals on-site, anywhere on the globe, with no cost or hazard risk of transportation when coupled with air capture of $CO_2$. The need for removing $CO_2$ from the air is coupled with an increasing global utilization of renewable electricity generation methods, such as solar photovoltaics and wind turbines. Techniques like these use intermittent energy sources, such as the sun, which sets in the evening and rises in the morning, and wind, which blows intermittently. Thus, the supply of electricity from these sources to electrical grids surges at some points, and is low at others. This presents an opportunity for technologies that can intermittently utilize electricity to produce desired products on-site.

Of the available technologies to produce chemicals from carbon dioxide, hydrogenation of carbon dioxide or carbon monoxide using renewably-derived hydrogen gas from a water electrolyzer is capable of being powered completely by renewable (solar, wind, hydroelectric, etc.) electricity. A method such as this converts a carbon-based feedstock (carbon dioxide or carbon monoxide) and water into hydrocarbon chemicals using an external energy source; this is similar to the fundamental photosynthetic processes enabling life on our planet. For example, plants use photosynthesis to convert carbon dioxide, water, and solar energy into chemical energy by creating sugars and other complex hydrocarbons. This effectively stores the energy from the sun in the chemical bonds of a carbon-based compound. This process has been supporting the Earth's ecosystem and balancing carbon dioxide concentration in our atmosphere for billions of years.

In the last century, human beings have harnessed byproducts of photosynthesis, such as fossil fuels, to provide the energy required for modern life. This has released millions of tons of carbon dioxide into the Earth's atmosphere that had been previously sequestered into the fossil fuels by photosynthesis over the course of millions of years. Scientific evidence points to this rapid increase in carbon dioxide concentration in the atmosphere from anthropogenic sources to be potentially catastrophic to global climate. The development of carbon-negative processes that mimic natural ones to sequester carbon dioxide are, therefore, critical to the future of the planet, and it is an object of the present application to disclose one such invention.

One of the major hurdles toward carbon dioxide sequestration is the effective utilization and catalytic transformation of carbon dioxide or carbon monoxide into useful chemicals. Plants achieve this via dehydrogenase enzymes, which utilize transition metals to catalyze the hydrogenation of carbon dioxide into carbon monoxide, formic acid, or a number of other building blocks for sugars. Man-made systems have attempted to copy this route, and chemical methods for carbon dioxide transformation have been known for decades. Many of these, however, have energy requirements unrealistic for any large-scale deployment.

In recent years, electrochemical methods such as water electrolysis have shown promise to reduce these energy requirements to practical levels. Advances in electrochemical methods enable three such options for carbon dioxide sequestration in chemicals powered by electricity that can be sourced in a low-carbon manner: (1) electrolytic carbon dioxide reduction for one-step production of chemicals directly from carbon dioxide, (2) combined electrolysis of water to form hydrogen and oxygen gas, with subsequent hydrogenation of carbon dioxide using hydrogen gas from the electrolyzer in a high pressure, high temperature reactor in a two-step process, and (3) electrolytic carbon dioxide reduction to an intermediate that can be combined with electrochemically-derived hydrogen in a high pressure, high temperature reactor. The former process requires significant development and an improved understanding of fundamental electrocatalytic processes for carbon dioxide reduction to reach commercial viability. Specific to the production of alcohols like ethanol, integrated chemical processes require traditionally fossil-fuel based components (such as methane), with few exceptions for production of alcohols (ethanol, methanol, propanols, butanols) for any feasible further use.

In any of these processes, a crucial component is the catalyst that converts the $CO_2$ and hydrogen gas or hydrogen equivalents. Catalysts for $CO_2$ conversion, specifically, face a major challenge in that $CO_2$ requires a substantial amount of energy to transform into other compounds. This makes stability and activity a key challenge for industrial catalysts for $CO_2$ conversion. Prior to the present disclosure, because of the lack of stable catalysts for this process, no commercial chemical process was known that converts carbon dioxide into alcohols without a separate step in a chemical process that converts $CO_2$ to CO or $CH_4$ (as in the Sabatier process).

SUMMARY OF THE INVENTION

In certain aspects, the present disclosure provides catalysts, comprising: copper; zinc; one or more first elements selected from iron, nickel, or cobalt; aluminum; oxygen; optionally, one or more second elements selected from a Group V, VI, VII, VIII, IX, X, and XI metal (e.g., manganese, silver, niobium, zirconium, molybdenum, ruthenium, or palladium); and optionally, one or more Group IA metals, and wherein the first element is present in an amount of about 1 to about 40 wt. % (e.g., about 1 to about 10 wt. %, about 25 to about 40 wt. %, about 30 to about 40 wt. %, or about 35 to about 40 wt. %) of the total amount of the copper, zinc, the first element, the optional second element, and the optional Group IA metal.

In certain aspects, the present disclosure provides CZA catalysts, comprising:

copper; zinc; optionally, one or more first elements selected from cobalt, iron, or nickel;

aluminum;

oxygen; optionally, one or more second elements selected from a Group V, VI, VII, VIII, IX, X, and XI metal (e.g., manganese, silver, niobium, zirconium, molybdenum, ruthenium, or palladium); and optionally, one or more Group IA metals; wherein the molar ratio of copper to zinc is from about 2 to about 4.

In certain aspects, the present disclosure provides catalytic compositions, comprising the catalysts disclosed herein and an additional support.

In certain aspects, the present disclosure provides methods of preparing the catalysts or catalytic compositions disclosed herein, such as methods comprising preparing the catalyst by coprecipitation, wet impregnation, or ball milling.

In certain aspects, the present disclosure provides methods of reducing $CO_2$ to a liquid product mixture, comprising contacting the catalysts or other catalytic compositions disclosed herein with a feed mixture comprising $CO_2$ and a reductant gas at a reduction temperature and a reduction pressure, thereby providing the liquid product mixture.

BRIEF DESCRIPTION OF THE DRAWINGS

FIG. 1 shows a plot demonstrating total mass of ethanol produced from $CO_2$ as a function of time in the presence of an exemplary CoFe-CZA (Cu(ZnO)CoFeK/Al$_2$O$_3$) catalyst compared to a CZA catalyst under identical conditions.

DETAILED DESCRIPTION OF THE INVENTION

Some catalysts for reduction of $CO_2$ have been demonstrated in academic literature, but none have transitioned to industrial use due to either high cost or poor stability. Ni-based catalysts are primarily used to hydrogenate $CO_2$ to $CH_4$. Co, Fe, Ru, Ir and Rh compounds can also be used as catalysts for these processes, as well as for higher order hydrocarbon formation. Several combinations of these elements in bimetallic and trimetallic catalysts have also been attempted. For the formation of alcohols, catalysts comprised of Rh, Pd, Cu, Zn, Co, or Ni, supported on alumina or carbon have also been studied. However, no catalysts based on low-cost metals listed above (such as Cu, Zn, Fe, Co, or Ni) suitable for large-scale commercial deployment (i.e., not Pt-group metals such as Ru, Ir, and Rh) have yet been demonstrated as commercial catalysts for the hydrogenation of $CO_2$ to alcohols. This is primarily because these compounds have not shown the stability that is required for scaling up the materials, since these catalysts decay into less active materials while on-stream in a reactor.

Catalysts made of copper with zinc oxide on an alumina scaffold, known as copper-zinc-alumina or "CZA" catalysts, are typically used for the production of methanol from carbon monoxide, a commodity chemical that is produced on the scale of millions of tons per year. CZA catalysts are also useful for the hydrogenation of $CO_2$ to methanol due to their high selectivity, but suffer from several other drawbacks such as product purity and limited catalyst lifetime. This high selectivity for methanol, however, hinders production of higher alcohols for situation where higher alcohols (such as ethanol) may be desired.

The present disclosure provides catalysts made of copper and zinc oxide on alumina (CZA) optionally doped with a metal selected from iron, nickel, or cobalt for $CO_2$ conversion to methanol, ethanol, and higher alcohols, as well as methods of using such catalysts for production of alcohols from $CO_2$. As further described herein, the catalysts of the present disclosure include first element (Co, Fe, Ni) as a metal promoting carbon-carbon bond formation. Previously, CZA catalysts had not been demonstrated as competent catalysts for $CO_2$ hydrogenation to multi-carbon alcohols, such as ethanol. Among other benefits, the modified CZA catalysts of the present disclosure catalyze the production of ethanol from carbonaceous feedstocks, $CO_2$, CO, or $CH_4$ at a higher rate than legacy CZA catalysts. These catalysts can also be used to inhibit the formation of gaseous byproducts during operation, e.g., $CH_4$, to further enable effective recycle of unreacted gases during product gas recycle in a multi-pass gas to liquids reactor for methanol production.

Catalysts

In certain aspects, the present disclosure provides catalysts, comprising: copper; zinc; one or more first elements selected from iron, nickel, or cobalt; aluminum; oxygen; optionally, one or more second elements selected from a Group V, VI, VII, VIII, IX, X, and XI metal (e.g., manganese, silver, niobium, zirconium, molybdenum, ruthenium, or palladium); and optionally, one or more Group IA metals, and wherein the first element is present in an amount of about 1 to about 40 wt. % (e.g., about 1 to about 10 wt. %, about 25 to about 40 wt. %, about 30 to about 40 wt. %, or about 35 to about 40 wt. %) of the total amount of the copper, zinc, cobalt, the optional second element, and the optional Group IA metal.

In some embodiments, the first element is present in an amount of about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, or about 40 wt. % of the total amount of the copper, zinc, the first element, the optional second element, and the optional Group IA metal. In some embodiments, the first element is present in an amount of 1-10 wt. %, 10-20 wt. %, or 20-30 wt. %, 20-25 wt. %, 22-24 wt. %, 25-40 wt. % 30-40 wt. %, or 35-40 wt. % of the total amount of the total amount of the copper, zinc, the first element, the optional second element, and the optional Group IA metal.

In some embodiments, the catalyst comprises a cobalt-embedded interconnected matrix of reduced copper metal nanoparticles and alumina-modified zinc oxide. In some embodiments, the cobalt is present as cobalt oxide. In some embodiments, the copper is present as copper oxide. In some embodiments, the molar ratio of cobalt to copper to zinc (Co:Cu:Zn) is about 0.5-3 in cobalt, 1-4 in copper, and 0.5-1.5 in zinc. In some embodiments, the Co:Cu:Zn ratio is in the range of 1-2 in cobalt, 1-3 in copper, and 0.5-1 in zinc. In some embodiments, the Co:Cu:Zn ratio is approximately 1:2.5:1. In some embodiments, the zinc is preferably 0.3-1 the molar content of the copper. In some embodiments, the cobalt is preferably 0.4-1 the molar content of the copper.

In some embodiments, the catalyst comprises a iron-embedded interconnected matrix of reduced copper metal nanoparticles and alumina-modified zinc oxide. In some embodiments, the iron is present as iron oxide. In some embodiments, the copper is present as copper oxide. In some embodiments, the molar ratio of iron to copper to zinc (Fe:Cu:Zn) is about 0.05-3 in iron, 1-4 in copper, and 0.5-1.5 in zinc. In some embodiments, the Fe:Cu:Zn ratio is in the range of 1-2 in iron, 1-3 in copper, and 0.5-1 in zinc. In some embodiments, the Fe:Cu:Zn ratio is approximately 1:2.5:1. In some embodiments, the zinc is preferably 0.3-1 the molar content of the copper. In some embodiments, the iron is preferably 0.4-1 the molar content of the copper.

In some embodiments, the catalyst comprises a nickel-embedded interconnected matrix of reduced copper metal nanoparticles and alumina-modified zinc oxide. In some embodiments, the nickel is present as nickel oxide. In some embodiments, the copper is present as copper oxide. In some embodiments, the molar ratio of nickel to copper to zinc (Ni:Cu:Zn) is about 0.5-3 in nickel, 1-4 in copper, and 0.5-1.5 in zinc. In some embodiments, the Ni:Cu:Zn ratio is in the range of 1-2 in nickel, 1-3 in copper, and 0.5-1 in zinc. In some embodiments, the Ni:Cu:Zn ratio is approximately 1:2.5:1. In some embodiments, the zinc is preferably 0.3-1 the molar content of the copper. In some embodiments, the nickel is preferably 0.4-1 the molar content of the copper.

In some embodiments, the catalyst comprises one or more elements selected from a transition, or Group VI, VII, VIII, IX, X, or XI metal. In some embodiments, the catalyst comprises one or more second elements selected from a Group VI metal. In some embodiments, the catalyst comprises one or more second elements selected from a Group VII metal. In some embodiments, the catalyst comprises one or more second elements selected from a Group VIII metal. In some embodiments, the catalyst comprises one or more second elements selected from a Group IX metal. In some embodiments, the catalyst comprises one or more second elements selected from a Group X metal. In some embodiments, the catalyst comprises one or more second elements selected from a Group XI metal.

In some embodiments, the one or more second elements comprise manganese, silver, niobium, zirconium, molybdenum, ruthenium, or palladium.

In some embodiments, the one or more second elements comprise iron. In some embodiments, the one or more second elements comprise nickel. In some embodiments, the one or more second elements comprise silver. In some embodiments, the one or more second elements comprise palladium. In some embodiments, the one or more second elements comprise niobium. In some embodiments, the one or more second elements comprise manganese. In some embodiments, the one or more second elements comprise zirconium. In some embodiments, the one or more second elements comprise molybdenum.

In some embodiments, the catalyst comprises the one or more second elements at a molar ratio of about 0.15 to about 2 relative to copper. In some embodiments, the catalyst comprises the one or more second elements at a molar ratio of about 0.15 to about 1.5 relative to copper. In some embodiments, the catalyst comprises the one or more second elements at a molar ratio of about 0.15 to about 1 relative to copper. In some embodiments, the catalyst comprises the one or more second elements at a molar ratio of about 0.15 to about 0.75 relative to copper. In some embodiments, the catalyst comprises the one or more second elements at a molar ratio of about 0.15 to about 0.5 relative to copper. In some embodiments, the catalyst comprises the one or more second elements at a molar ratio of about 0.15 to about 0.25 relative to copper.

In some embodiments, the catalyst comprises copper at a molar ratio of about 0.5 to about 5 relative to zinc. In some embodiments, the catalyst comprises copper at a molar ratio of about 1 to about 3 relative to zinc. In some embodiments, the catalyst comprises copper at a molar ratio of about 2 to about 2.5 relative to zinc. In some embodiments, the catalyst comprises copper at a molar ratio of about 2.33 relative to zinc. In some embodiments, the catalyst comprises copper at a molar ratio of about 0.75 to about 1.5 relative to zinc. In some embodiments, the catalyst comprises copper at a molar ratio of about 1.5 relative to zinc. In some embodiments, the catalyst comprises copper at a molar ratio of about 1.0 relative to zinc. In some embodiments, the catalyst comprises copper at a molar ratio of about 0.75 relative to zinc. In some embodiments, the catalyst comprises copper at a molar ratio of about 0.5 relative to zinc.

In some embodiments, the catalyst comprises zinc at a molar ratio of about 0.3 to about 3 relative to copper. In some embodiments, the catalyst comprises zinc at a molar ratio of about 0.5 to about 2 relative to copper. In some embodiments, the catalyst comprises zinc at a molar ratio of about 0.5 to about 1.5 relative to copper. In some embodiments, the catalyst comprises zinc at a molar ratio of about 1.5 relative to copper. In some embodiments, the catalyst comprises zinc at a molar ratio of about 1.0 relative to copper. In some embodiments, the catalyst comprises zinc at a molar ratio of about 0.75 relative to copper. In some embodiments, the catalyst comprises zinc at a molar ratio of about 0.5 relative to copper.

In some embodiments, the one or more second elements comprise niobium. In some embodiments, the one or more second elements consist of niobium. In some embodiments, the niobium is present at a molar ratio of about 0.05 to about 1 relative to copper. In some embodiments, the niobium is present at a molar ratio of about 0.2 relative to copper. In some embodiments, the niobium is present at a molar ratio of about 0.3 relative to copper. In some embodiments, the niobium is present at a molar ratio of about 0.1 relative to copper.

In some embodiments, the catalyst comprises the one or more Group IA metals. In some embodiments, the catalyst comprises the one or more Group IA metals at a molar ratio from about 0.01 to about 1.0 relative to copper. In some embodiments, the catalyst comprises the one or more Group IA metals at a molar ratio from about 0.05 to about 0.50 relative to copper. In some embodiments, the catalyst comprises the one or more Group IA metals at a molar ratio from about 0.20 to about 0.50 relative to copper. In some embodiments, the catalyst comprises the one or more Group IA metals at a molar ratio from about 0.30 to about 0.50 relative to copper. In some embodiments, the catalyst comprises the one or more Group IA metals at a molar ratio from about 0.40 to about 0.50 relative to copper. In some embodiments, the catalyst comprises the one or more Group IA metals at a molar ratio at about 0.15 relative to copper.

In some embodiments, the catalyst comprises one or more Group IA metals. In some embodiments, the one or more Group IA metals comprise potassium, sodium or cesium. In some embodiments, the one or more Group IA metals consist of potassium, sodium or cesium. In some embodiments, the one or more Group IA metals comprise potassium. In some embodiments, the one or more Group IA metals comprise sodium. In some embodiments, the one or more Group IA metals comprise cesium. In some embodiments, the one or more Group IA metals consist of potassium. In some embodiments, the one or more Group IA metals consist of sodium. In some embodiments, the one or more Group IA metals consist of cesium.

In some embodiments, the catalyst comprises potassium at a molar ratio of about 0.05, about 0.1, about 0.15, about 0.2, about 0.25, about 0.3, about 0.35, about 0.4, about 0.45, or about 0.5 relative to copper. In some embodiments, the catalyst comprises potassium at a molar ratio of about 0.15 relative to copper.

In some embodiments, the catalyst comprises aluminum at a molar ratio of about 0.1 to about 10 relative to copper. In some embodiments, the catalyst comprises aluminum at a molar ratio of about 0.1 to about 5 relative to copper. In some embodiments, the catalyst comprises aluminum at a molar ratio of about 0.4 to about 2.1 relative to copper. In some embodiments, the catalyst comprises aluminum at a molar ratio of about 0.5 to about 1 relative to copper.

In some embodiments, the catalyst comprises zinc oxide.

In some embodiments, the catalyst comprises copper oxide.

In some embodiments, the catalyst comprises cobalt oxide.

In some embodiments, the catalyst comprises iron oxide.

In some embodiments, the catalyst comprises nickel oxide.

In some embodiments, the catalyst comprises alumina.

In certain embodiments, the one or more Group IA metals comprise or consist of sodium or cesium. In the catalysts of the present disclosure, substituting sodium or cesium for potassium does not substantially affect the catalytic activity, and both sodium and cesium have been found to provide the same stability potassium provides. This is a contrast with known syngas catalysts, where the choice of potassium, sodium or cesium greatly affects activity.

In some embodiments, the catalyst comprises or consists of aluminum oxide ($Al_2O_3$) wherein the aluminum is present in a molar ratio of about 0.02 to about 3 relative to copper. In some embodiments, the aluminum is present in a molar ratio of about 0.1 to about 0.8 relative to copper. In some embodiments, the aluminum is present in a molar ratio of about 0.7 relative to copper. In some embodiments, the alumina can be added as a support to increase the surface area of the copper and zinc, or produced in-situ as a component of the catalyst, e.g. from aluminum nitrate co-precipitation with first element, copper, and zinc precursors.

In some embodiments, the catalyst comprises copper, zinc oxide, cobalt, and alumina. In some such embodiments, the molar ratios of the components are as described above. In some embodiments, the catalyst comprises: cobalt; copper at a molar ratio of about 2.5 relative to the cobalt; zinc at a molar ratio of about 1 relative to the cobalt, and alumina, with the aluminum at a molar ratio of about 0.7 relative to cobalt. In some embodiments, the catalyst comprises: copper at a molar ratio of about 2.5 relative to the cobalt; zinc oxide at a molar ratio of about 1 relative to the cobalt; and alumina at a molar ratio of about 0.35 relative to the cobalt.

In some embodiments, the catalyst comprises copper, zinc oxide, nickel, and alumina. In some such embodiments, the molar ratios of the components are as described above. In some embodiments, the catalyst comprises: nickel; copper at a molar ratio of about 2.5 relative to the nickel; zinc at a molar ratio of about 1 relative to the cobalt, and alumina, with the aluminum at a molar ratio of about 0.7 relative to nickel. In some embodiments, the catalyst comprises: copper at a molar ratio of about 2.5 relative to the nickel; zinc oxide at a molar ratio of about 1 relative to the nickel; and alumina at a molar ratio of about 0.35 relative to the nickel.

In some embodiments, the catalyst comprises copper, zinc oxide, iron, and alumina. In some such embodiments, the molar ratios of the components are as described above. In some embodiments, the catalyst comprises: iron; copper at a molar ratio of about 2.5 relative to the iron; zinc at a molar ratio of about 1 relative to the iron, and alumina, with the aluminum at a molar ratio of about 0.7 relative to iron. In some embodiments, the catalyst comprises: copper at a molar ratio of about 2.5 relative to the iron; zinc oxide at a molar ratio of about 1 relative to the iron; and alumina at a molar ratio of about 0.35 relative to the iron.

In some embodiments, the catalyst comprises copper, zinc oxide, cobalt, alumina, and a Group IA metal. In some embodiments, the molar ratios of the components are as described above. In some embodiments, the catalyst comprises: cobalt; copper at a molar ratio of about 2.5 relative to the cobalt; zinc at a molar ratio of about 1 relative to the cobalt; alumina, with the aluminum at a molar ratio of about 0.7 relative to the cobalt; and the Group IA at a molar ratio of about 0.1 relative to the cobalt. In some embodiments, the catalyst comprises: copper at a molar ratio of about 2.5 relative to the cobalt; zinc oxide at a molar ratio of about 1 relative to the cobalt; alumina at a molar ratio of about 0.35 relative to the cobalt; and the Group IA metal at a molar ratio of about 0.1 relative to the cobalt.

In some embodiments, the catalyst comprises copper, zinc oxide, nickel, alumina, and a Group IA metal. In some embodiments, the molar ratios of the components are as described above. In some embodiments, the catalyst comprises: nickel; copper at a molar ratio of about 2.5 relative to the nickel; zinc at a molar ratio of about 1 relative to the nickel; alumina, with the aluminum at a molar ratio of about 0.7 relative to the nickel; and the Group IA at a molar ratio of about 0.1 relative to the nickel. In some embodiments, the catalyst comprises: copper at a molar ratio of about 2.5 relative to the nickel; zinc oxide at a molar ratio of about 1 relative to the nickel; alumina at a molar ratio of about 0.35 relative to the nickel; and the Group IA metal at a molar ratio of about 0.1 relative to the nickel.

In some embodiments, the catalyst comprises copper, zinc oxide, iron, alumina, and a Group IA metal. In some embodiments, the molar ratios of the components are as described above. In some embodiments, the catalyst comprises: iron; copper at a molar ratio of about 2.5 relative to the iron; zinc at a molar ratio of about 1 relative to the iron; alumina, with the aluminum at a molar ratio of about 0.7 relative to the iron; and the Group IA at a molar ratio of about 0.1 relative to the iron. In some embodiments, the catalyst comprises: copper at a molar ratio of about 2.5 relative to the iron; zinc oxide at a molar ratio of about 1 relative to the iron; alumina at a molar ratio of about 0.35 relative to the iron; and the Group IA metal at a molar ratio of about 0.1 relative to the iron.

In some embodiments, the catalyst comprises Cu, Zn, Al, O, and an alkali metal. In some embodiments, the catalyst comprises Cu, Zn, Ni, Al, O, and an alkali metal. In some embodiments, the catalyst comprises Cu, Zn, Fe, Al, O, and an alkali metal. In some embodiments, the catalyst comprises Cu, Zn, Co, Fe, Al, O, and an alkali metal. In some embodiments, the catalyst comprises Cu, Zn, Co, Al, O, and an alkali metal. In some embodiments, the catalyst comprises Cu, Zn, Co, Nb, Al, and O, and an alkali metal. In some embodiments, the catalyst comprises Cu, Zn, Co, Ni, Al, and O, and an alkali metal. In some embodiments, the catalyst comprises Cu, Zn, Co, Mo, Al, and O, and an alkali metal.

In some embodiments, the catalyst comprises Cu, Zn, Al, and O. In some embodiments, the catalyst comprises Cu, Zn, Fe, Al, and O. In some embodiments, the catalyst comprises Cu, Zn, Ni, Al, and O. In some embodiments, the catalyst comprises Cu, Zn, Co, Al, and O. In some embodiments, the catalyst comprises Cu, Zn, Co, Fe, Al, and O.

In some embodiments, the catalyst comprises Cu, Zn, Co, Nb, Al, and O. In some embodiments, the catalyst comprises Cu, Zn, Co, Ni, Al, and O. In some embodiments, the catalyst comprises Cu, Zn, Co, Mo, Al, and O.

In certain embodiments, the elemental composition of the catalyst material is $Cu(ZnO)CoA/Al_2O_3$, $Cu(ZnO)CoFeA/Al_2O_3$, $Cu(ZnO)CoNbA/Al_2O_3$, $Cu(ZnO)CoNiA/Al_2O_3$, $Cu(ZnO)CoMoA/Al_2O_3$ wherein A is an alkali metal and further wherein the relative amounts of the elemental components are as described above.

In certain embodiments, the elemental composition of the catalyst material is $Cu(ZnO)Co/Al_2O_3$, $Cu(ZnO)CoFe/Al_2O_3$, $Cu(ZnO)CoNb/Al_2O_3$, $Cu(ZnO)CoNi/Al_2O_3$, $Cu(ZnO)CoMo/Al_2O_3$, wherein the relative amounts of the elemental components are as described above.

In some embodiments, the catalyst is selected from one of the following exemplary catalysts: CuO(ZnO), Cu(ZnO)Co, Cu(ZnO)CoK, Cu(ZnO)CoFe, Cu(ZnO)CoFeK, Cu(ZnO)CoNi, Cu(ZnO)CoNiK, Cu(ZnO)CoNb, Cu(ZnO)CoNbK, Cu(ZnO)CoMo, Cu(ZnO)CoMoK on $Al_2O_3$, wherein the relative amounts of the elemental components are as described above. In certain such embodiments, the catalyst is approximately $CuO_{(2)}(ZnO)_{(1)}$, $Cu_{(2.5)}(ZnO)_{(1)}Co_{(1)}$, $Cu_{(2.5)}(ZnO)_{(1)}Co_{(1)}K_{(0.1)}$, $Cu_{(1)}(ZnO)_{(1)}Co_{(1)}Fe_{(1)}$, $Cu_{(1)}(ZnO)_{(1)}Co_{(1)}Fe_{(1)}K_{(0.15)}$, $Cu_{(2)}(ZnO)_{(1)}Co_{(1)}Ni_{(1)}$, $Cu_{(2)}(ZnO)_{(1)}Co_{(1)}Ni_{(1)}K_{(0.15)}$, $Cu_{(2)}(ZnO)_{(1)}Co_{(1)}Nb_{(1)}$, $Cu_{(2)}(ZnO)_{(1)}Co_{(1)}Nb_{(1)}K_{(0.15)}$, $Cu_{(2)}(ZnO)_{(1)}Co_{(1)}Mo_{(1)}$, $Cu_{(2)}(ZnO)_{(1)}Co_{(1)}Mo_{(1)}K_{(0.15)}$.

Catalytic Compositions

In certain aspects, the present disclosure provides catalytic compositions, comprising one or more of the catalysts disclosed herein and an additional support. The additional support may be any suitable material that can serve as a catalyst support.

In some embodiments, the additional support comprises one or more materials selected from an oxide, nitride, fluoride, or silicate of an element selected from aluminum, silicon, titanium, zirconium, cerium, magnesium, yttrium, lanthanum, zinc, and tin. In some preferred embodiments, the additional support comprises γ-alumina. In some embodiments, the additional support is an aluminum oxide that is formed in-situ as part of the catalyst. In some embodiments, the additional support is selected from, but not limited to, $Al_2O_3$, $ZrO_2$, $SnO_2$, $SiO_2$, ZnO, and $TiO_2$. In some embodiments, the additional support is selected from $Al_2O_3$, $ZrO_2$, $SnO_2$, $SiO_2$, ZnO, and $TiO_2$.

In some embodiments, the additional support comprises one or more carbon-based materials. In some embodiments, the carbon-based material is selected from activated carbon, carbon nanotubes, graphene and graphene oxide.

In some embodiments, the additional support is a mesoporous material. In some embodiments, the additional support has a mesopore volume from about 0.01 to about 3.0 cc/g.

In some embodiments, the additional support has surface area from about 10 $m^2/g$ to about 1000 $m^2/g$. In some preferred embodiments, the catalytic composition comprising the additional support and a catalyst disclosed herein has a surface area from about 10 $m^2/g$ to about 1000 $m^2/g$.

In some embodiments, the catalytic composition is in a form of particles having an average size from about 10 nm to about 5 μm. In some embodiments, the catalytic composition is in a form of particles having an average size from about 20 nm to about 5 μm. In some embodiments, the catalytic composition is in a form of particles having an average size from about 50 nm to about 1 μm. In some embodiments, the catalytic composition is in a form of particles having an average size from about 100 nm to about 500 nm. In some embodiments, the catalytic composition is in a form of particles having an average size from about 50 nm to about 300 nm.

In some embodiments, the catalytic composition comprises from about 5 wt. % to about 80 wt. % of the catalyst. In some embodiments, the catalytic composition comprises from about 5 wt. % to about 70 wt. % of the catalyst. In some embodiments, the catalytic composition comprises from about 20 wt. % to about 70 wt. % of the catalyst. In some embodiments, the catalytic composition comprises from about 30 wt. % to about 70 wt. % of the catalyst.

In some embodiments, the support is a high surface area scaffold. In some embodiments, the support comprises mesoporous silica. In some embodiments, the support comprises carbon allotropes.

In some embodiments, the catalyst is a nanoparticle catalyst. In some embodiments, the particle sizes of the catalyst on the surface of the scaffold are 100-500 nm. In some embodiments, the particles not subjected to agglomeration are 100-500 nm in particle size.

Methods of Preparation

The catalysts and catalytic compositions of the present disclosure may be prepared by any suitable method. In certain aspects, the present disclosure provides methods for preparing the catalysts or the catalytic compositions disclosed herein, comprising preparing the catalyst by coprecipitation, wet impregnation, or ball milling.

In some embodiments, the method comprises the following steps:

(a) providing a first solution comprising a source of cobalt, copper, zinc, aluminum, a base, and water;

(b) heating the first solution at a first temperature for a first period of time, thereby producing the first reaction mixture;

(c) heating the first reaction mixture at a second temperature for a second period of time to remove the water, thereby producing a solid precursor; and (d) heating the solid precursor to a third temperature for a third period of time, thereby isolating the catalyst.

In some embodiments, the method comprises the following steps:

(a) providing a second solution comprising a source of cobalt, copper, zinc, iron, and water;

(b) providing a third solution comprising a base;

(c) heating the third solution at a third temperature for a third period of time;

(d) adding alumina to the third solution, thereby producing a second reaction mixture;

(e) adding the second solution to the second reaction mixture at a fourth temperature for a fourth period of time, thereby producing a third reaction mixture;

(f) heating the third reaction mixture at a fifth temperature for a fifth period of time, thereby producing a solid precursor;

(g) isolating the solid precursor;

(h) contacting the solid precursor with a solution comprising a Group IA metal, thereby producing a catalyst precursor; and (i) heating the catalyst precursor to a sixth temperature for a sixth period of time, thereby isolating the catalyst.

In some embodiments, the method comprises the following steps: providing a first solution comprising a source of cobalt, a source of copper, a source of zinc, and a source of aluminum. Combining the first solution with a basic precipitant, such as a carbonate, to increase the pH of the metal salt containing solution thereby precipitating solid particles. The solid particles are dried and calcined to form a solid catalyst.

In some embodiments, the method comprising the following steps: providing a first solution comprising a cobalt source and introducing it to a pre-made copper-zinc alumina material via incipient wetness or wet impregnation, followed by drying and calcining to form a solid catalyst.

In some embodiments, the method comprising the following steps: mixing a cobalt source and a support in a mill jar to provide a first mixture; ball milling the first mixture for between 2 hours to 2 weeks to thereby provide a first precipitate; filtering the first precipitate and heating to a first temperature to provide a ball milled cobalt source; mixing the ball milled cobalt source with a source of copper and zinc and a source of the alumina to provide a second mixture; and isolating a solid material from the second mixture.

In some embodiments, the method further comprises combining the solid material with a source of the one or more Group IA metals. In some embodiments, the method further comprises pressing the solid material into pellets. In some embodiments, the method further comprises pressing the solid material into pellets prior to introduction into a flow reactor.

Methods of Hydrogenation

In certain aspects, the present disclosure provides methods of reducing carbonaceous feedstock, namely $CO_2$ to a liquid product mixture, comprising contacting the catalysts of catalytic compositions disclosed herein with a feed mixture comprising $CO_2$ and a reductant gas at a reduction temperature and a reduction pressure, thereby providing the liquid product mixture.

In some embodiments, the reductant gas is $H_2$. In some embodiments, the reductant gas is a hydrocarbon, such as $CH_4$, ethane, propane, or butane. In preferred embodiments, the hydrocarbon is $CH_4$. In certain such embodiments, the $CH_4$ is a component of a gas mixture that also comprises other hydrocarbons, such as ethane, propane, or butane. For example, the gas mixture used to supply $CH_4$ may be (or may be derived from) flare gas, waste gas, natural gas, or the like.

In some embodiments, the feed mixture further comprises CO. In some embodiments, the feed mixture comprises less than 25% of CO, less than 20% of CO, less than 15% of CO, less than 10% of CO, less than 5% of CO, or less than 1% of CO. In some embodiments, the feed mixture is substantially free of CO.

In some embodiments, the reduction temperature is from about 100 to about 450° C. In some embodiments, the reduction temperature is from about 275 to about 350° C. In some embodiments, the reduction temperature is about 275° C. In some embodiments, the reduction temperature is about 310° C.

In some embodiments, the reduction pressure is from about 50 to about 3000 psi. In some embodiments, the reduction pressure is from about 900 to about 1100 psi. In some embodiments, the reduction pressure is about 1000 psi.

In some embodiments, the partial pressure of $CO_2$ in the feed mixture is from about 20 to about 1000 psi. In some embodiments, the partial pressure of $CO_2$ in the feed mixture is from about 200 to about 800 psi, from about 200 to about 600 psi, from about 200 to about 400 psi, or from about 300 to about 400 psi. For example, the partial pressure of $CO_2$ in the feed mixture is about 200 psi, about 250 psi, about 300 psi, about 350 psi, about 400 psi, about 450 psi, about 500 psi, about 550 psi, about 600 psi, about 650 psi, about 700 psi, about 750 psi, about 800 psi, about 850 psi, about 900 psi, about 950 psi, or about 1000 psi. In some embodiments, the partial pressure of $CO_2$ in the feed mixture is about 330 psi.

In some embodiments, the ratio of reductant gas:$CO_2$ in the feed mixture is about 10:1 to about 1:10. In some embodiments, the ratio of reductant gas:$CO_2$ in the feed mixture is about 5:1 to about 0.5:1. In some embodiments, the ratio of reductant gas:$CO_2$ in the feed mixture is about 4:1 to about 1:1. In some embodiments, the ratio of reductant gas:$CO_2$ in the feed mixture is about 3:1.

In some embodiments, the liquid product mixture comprises methanol. In some embodiments, the liquid product mixture comprises methanol, ethanol, and n-propanol. In some embodiments, the liquid product mixture comprises methanol, ethanol, acetic acid, and n-propanol. In some embodiments, the amount of ethanol is at least 10 wt. % of the total In some embodiments, the amount of ethanol is at least 7 wt. % of the total amount of liquid product mixture. In some embodiments, the amount of ethanol is at least 5 wt. % of the total amount of liquid product mixture. In some embodiments, the amount of ethanol is at least 2 wt. % of the total amount of liquid product mixture. In some embodiments, the molar ratio of ethanol to the total amount of methanol and n-propanol in the liquid product mixture is from about 1:5 to about 1:10. In some embodiments, the amount of formic acid in the liquid product mixture is less than 10 ppm. In some embodiments, the amount of isopropanol in the liquid product mixture is less than 10 ppm.

It is an object of the present invention to use low GHSVs (gas hourly space velocity) to provide high gas product recyclability and avoid certain byproducts such as formaldehyde. In some embodiments, the method does not produce formaldehyde. In some embodiments, the method produces less than about 0.05 wt % formaldehyde. In some embodiments, the method produces less than about 50 ppm formaldehyde. In some embodiments, the method produces less than 5 ppm formaldehyde.

In some embodiments, the GHSV of reactant gases and recycle gases introduced to the reactor is 10. In some embodiments, the GHSV of reactant gases and recycle gases introduced to the reactor is 100. In some embodiments, the GHSV of reactant gases and recycle gases introduced to the reactor is 500. In some embodiments, the GHSV of reactant gases and recycle gases introduced to the reactor is 1,000. In some embodiments, the GHSV of reactant gases and recycle gases introduced to the reactor is 2,000. In some embodiments, the GHSV of reactant gases and recycle gases introduced to the reactor is 5,000. In some embodiments, the GHSV of reactant gases and recycle gases introduced to the reactor is 10,000. In some embodiments, the GHSV of reactant gases and recycle gases introduced to the reactor is 20,000.

In some embodiments, the GHSV of reactant gases and recycle gases introduced to the reactor is from about 10 to about 20,000. In some embodiments, the GHSV of reactant gases and recycle gases introduced to the reactor is from about 10 to about 10,000. In some embodiments, the GHSV of reactant gases and recycle gases introduced to the reactor is from about 10 to about 5,000. In some embodiments, the GHSV of reactant gases and recycle gases introduced to the reactor is from about 10 to about 2,000. In some embodiments, the GHSV of reactant gases and recycle gases introduced to the reactor is from about 10 to about 1,000. In some embodiments, the GHSV of reactant gases and recycle gases introduced to the reactor is from about 10 to about 500. In some embodiments, the GHSV of reactant gases and recycle gases introduced to the reactor is from about 10 to about 100.

In some embodiments, the GHSV of reactant gases and recycle gases introduced to the reactor is less than about 10. In some embodiments, the GHSV of reactant gases and recycle gases introduced to the reactor is less than about 100. In some embodiments, the GHSV of reactant gases and recycle gases introduced to the reactor is less than about 500. In some embodiments, the GHSV of reactant gases and recycle gases introduced to the reactor is less than about 1,000. In some embodiments, the GHSV of reactant gases and recycle gases introduced to the reactor is less than about 2,000. In some embodiments, the GHSV of reactant gases and recycle gases introduced to the reactor is less than about 5,000. In some embodiments, the GHSV of reactant gases and recycle gases introduced to the reactor is less than about 10,000. In some embodiments, the GHSV of reactant gases and recycle gases introduced to the reactor is less than about 20,000.

In some embodiments, the GHSV of reactant gases and recycle gases introduced to the reactor is 100. In some embodiments, the GHSV of reactant gases and recycle gases introduced to the reactor is 500. In some embodiments, the GHSV of reactant gases and recycle gases introduced to the reactor is 1,000. In some embodiments, the GHSV of reactant gases and recycle gases introduced to the reactor is 2,000. In some embodiments, the GHSV of reactant gases and recycle gases introduced to the reactor is 5,000. In some embodiments, the GHSV of reactant gases and recycle gases introduced to the reactor is 10,000. In some embodiments, the GHSV of reactant gases and recycle gases introduced to the reactor is 20,000.

In some embodiments, the method comprises contacting the catalyst with the feed mixture for at least 168 hours. In some embodiments, the method comprises contacting the catalyst with the feed mixture for at least 96 hours. In some embodiments, the method comprises contacting the catalyst with the feed mixture for at least 24 hours.

In some embodiments, the numbers used to describe and claim certain embodiments of the disclosure are modified in some instances by the term "about." In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In certain embodiments, the term "about" means within 10%, 9%, 8%, 7%, 6%, 5%, 4%, 3%, 2, 1%, 0.5%, or 0.05% of a given value or range.

EXAMPLES

The invention now being generally described, it will be more readily understood by reference to the following examples which are included merely for purposes of illustration of certain aspects and embodiments of the present invention, and are not intended to limit the invention.

Example 1: Synthesis of Co-CZA, Ni-CZA, and Fe-CZA Catalysts by Coprecipitation Co-CZA or Ni-CZA:

Cobalt nitrate or nickel nitrate (2 molar equivalent), zinc nitrate (1 molar equivalent), copper nitrate (3 molar equivalents), aluminum nitrate (1.4 molar equivalents), and sodium carbonate (9.7 molar equivalents) are combined in distilled water. The resulting mixture is stirred rapidly and heated at 70-90° C. for 2 hours, then dried at 120° C. overnight to remove water. The resulting solid material is dried under air at 110° C. for 12 hours, and the resulting solid material is crushed, heated to 350° C. in air at a heating rate of 2° C./min, and calcined at 350° C. for 6 h. After calcining, the resulting power was then further ground with a mortar and pestle.

Fe-CZA:

Ferric nitrate (1 molar equivalent), zinc nitrate (1 molar equivalent), copper nitrate (3 molar equivalents), aluminum nitrate (1.4 molar equivalents), and sodium carbonate (9.1 molar equivalents) are combined in distilled water. The resulting mixture is stirred rapidly and heated at 70-90° C. for 2 hours, then dried at 120° C. overnight to remove water. The resulting solid material is dried under air at 110° C. for 12 hours, and the resulting solid material is crushed, heated to 350° C. in air at a heating rate of 2° C./min, and calcined at 350° C. for 6 h. After calcining, the resulting power was then further ground with a mortar and pestle.

Example 2: Synthesis of Co-CZA, Fe-CZA, or Ni-CZA Catalysts by Wet Impregnation Wet impregnation (a.k.a. incipient wetness) synthesis: 40 grams of a copper-zinc oxide on alumina catalyst is contacted with a solution of $Co(NO_3)_2 \cdot 6H_2O$ (25 g in 50 mL of water), $Fe(NO_3)_3 \cdot 9H_2O$ (25 g in 50 mL of water), or $Ni(NO_3)_2 \cdot 6H_2O$ (25 g in 50 mL of water), wherein the metal-containing liquid is adsorbed into the alumina by capillary action and allowed to dry for a set period of time, typically 24 h, or in an oven at 120° C. for 12 h. The impregnated, dried sample is then ground to a powder with a mortar and pestle, heated to 350° C. at a heating rate of 2° C./min, and calcined in air at 350° C. for 6 h.

Example 3: Synthesis of Co-CZA Catalysts by Mechanical Activation

Mechanical activation synthesis: 50 g of copper-zinc oxide on alumina is mixed with 10 g of cobalt oxide and loaded in a 0.4 L mill jar filled ⅔ of the volume with 6.5 mm size of cylindrical grinding media, the grinding media possessing a total mass of 825 g. The mill jar is placed in a roller equipped with a ¼ horsepower motor and the ball milling process is conducted with 200 rpm of rolling speed for different durations, between 2 hours and two weeks.

Example 4: Synthesis of $Cu_{(1)}ZnO_{(1)}Co_{(1)}$ $Fe_{(1)}K_{(0.15)}$ on $Al_2O_3$ $Cu(NO_3)_3 \cdot 3H_2O$ (60 mmol, 14.5 g), $Zn(NO_3)_2 \cdot 6H_2O$ (60 mmol, 17.8 g), $Co(NO_3)_2 \cdot 6H_2O$ (60 mmol, 17.5 g) $Fe(NO_3)_3 \cdot 9H_2O$ (60 mmol, 24.2 g) were dissolved in 100 mL DI water to form a metal salt solution. $Na_2CO_3$ (180 mmol, 19.1 g) was dissolved in 150 mL DI water and heated to 60° C. γ-Al$_2$O$_3$ (231 mmol, 23.6 g) was added to the clear Na$_2$CO$_3$ aqueous solution. The metal salt solution was added to Na$_2$CO$_3$/Al$_2$O$_3$ mixture dropwise over 30 min. Additional Na$_2$CO$_3$ (45 mmol, 4.8 g) was added to solution mixture at 60° C. The mixture was heated at 70° C. for 1.5 hours while stirring and cooled down to room temperature. The solid precipitate was filtered and washed with DI water, then dried under air overnight and impregnated with K$_2$CO$_3$ (4.5 mmol, 0.62 g in 15 mL DI water). The resulting wet powder was agitated for 1 hour in a mechanical shaker, and the catalyst was dried under air at 110° C. for 12 hours. The resulting powder was crushed with a mortar and pestle heated to 350° C. in air at a heating rate of 2° C./min, and calcined under air at 350° C. for 6 hours, followed by additional grinding with a mortar and pestle.

Example 5: CO$_2$ Reduction in the Presence of Cu$_{(1)}$ZnO$_{(1)}$Co$_{(1)}$Fe$_{(1)}$K$_{(0.15)}$ on Al$_2$O$_3$ CO$_2$ reduction in the presence of Cu$_{(1)}$ZnO$_{(1)}$Co$_{(1)}$ Fe$_{(1)}$K$_{(0.15)}$ on Al$_2$O$_3$ was performed over a course of 5 days under the following conditions:

2:1 H$_2$:CO$_2$ ratio;
GHSV was 1000 h$^{-1}$;
CO$_2$ conversion per pass about 18%;
Temperature 310° C.;
Pressure 1000 psi.

Composition of the liquid product fraction at different time points during the course of the reaction is shown in Table 1.

TABLE 1

| Composition of the liquid product fraction in CO$_2$ reduction in the presence of Cu$_{(1)}$ZnO$_{(1)}$Co$_{(1)}$Fe$_{(1)}$K$_{(0.15)}$ on Al$_2$O$_3$. | | | | | | | |
|---|---|---|---|---|---|---|---|
| Time, h | Amount | Ethanol | Meth-anol | Acetic acid | Formic acid | Acetone | n-Propanol |
| 24 | g | 0.055 | 0.220 | 0.002 | 0.000 | 0.000 | 0.011 |
| 48 | g | 0.043 | 0.219 | 0.002 | 0.000 | 0.000 | 0.009 |
| 72 | g | 0.050 | 0.242 | 0.001 | 0.000 | 0.000 | 0.010 |
| 96 | g | 0.058 | 0.284 | 0.001 | 0.000 | 0.000 | 0.013 |
| 120 | g | 0.037 | 0.226 | 0.000 | 0.000 | 0.000 | 0.008 |

Example 6: Catalytic Reduction of CO$_2$ to Alcohols Using CH$_4$ as a Reductant For catalyst screening experiments, a CZA catalyst is loaded into a 600 mL continuously stirred tank reactor. The catalyst is optionally activated with H$_2$ prior to the start of the run. To activate the catalyst, the reactor is flushed with H$_2$ gas prior to being filled to 300 psi of H$_2$ for catalyst activation. Catalyst activation occurs at a pressure of at least 100 psi, where the reactor is heated at 300° C. for 1.0 hour, then cooled down to 25° C., with a heating ramp rate of 6° C./min and cooling ramp rate of around –6° C./min. The reactor is vented, then flushed with 250 psi of CO$_2$. The reactor is filled with CO$_2$ to 250 psi and 500 psi of CH$_4$ leading to a total pressure at 750 psi. The reactor is then heated to 250° C. for 15 hours prior to cooling and product collection. For product collection, the reactor is vented and disassembled to recover liquid at the bottom of the reactor. The liquid is washed and filtered to remove excess catalyst. The liquid is analyzed by gas chromatography (GC) to determine methanol, ethanol, n-propanol, and higher alcohol content to assess whether the catalyst is capable of producing alcohols using CO$_2$ and CH$_4$.

For alcohol production using the catalysts disclosed in this specification, a tubular fixed bed flow reactor is typically used, but other reactor types may also be used. For the example of a tubular fixed bed flow reactor, the optimal reactor temperature is between 200° C. and 300° C., but may vary between 100° C. and 450° C. A half-inch diameter, three foot long vertical tubular reactor is loaded with 5 mL of a mixture of catalyst powder and, optionally, inert alumina to even out temperature differences within the reactor during exothermal operation. The feed ratio of gases is 2:1 CH$_4$:CO$_2$, but can vary from 10:1 CH$_4$:CO$_2$ to 1:10 CH$_4$: CO$_2$, optionally with the presence of other carbonaceous gases such as CO. The gas hourly space velocity (GHSV) in the present example is 1000 h$^{-1}$, but can vary from 100 h$^{-1}$ to 75,000 h$^{-1}$. In some cases, gases that are unreacted in their first pass through the reactor may be recycled from the reactor back into the inlet. The pressure of the reactor is 1000 psi, however the pressure may vary from 500 psi to 5000 psi. There are sometimes no requirements for catalyst conditioning in these reaction systems, however, some catalysts may require heating to temperatures as high as 400° C. under at least 100 psi of H$_2$, CO, or CH$_4$ gas for up to 24 hours. Once CH$_4$ and CO$_2$ gases begin flowing and the reaction starts, it takes approximately 12 hours for the system to stabilize into a steady state where alcohol production levels off and is no longer increasing or decreasing.

Example 7: Catalytic Reduction of CO$_2$ to Mixed Alcohols Using a Co-CZA Catalyst For alcohol production, the reactor pressure is increased to 1000 psi and temperature decreased to 235° C. Approximately 0.3 kg/h H$_2$ and 3.5 kg/h CO$_2$ are flowed into the reactor system and reacted over the catalyst, followed by product gas cooling and condensation of the room temperature liquids in a separator vessel, with gaseous byproducts and unreacted CO$_2$ and H$_2$ recycled back into the reactor inlet. Approximately 1 gallon per hour of product liquid was produced with an alcohol content of approximately 40% methanol and 2% ethanol in water. The relative concentration of ethanol and methanol in water was variable based on the flow rate and feed ratio of inlet CO$_2$ and H$_2$. Minimal higher alcohol production (n-propanol and higher) was observed, with no detectable presence of branched higher alcohols (isopropanol) by gas chromatography coupled with mass spectroscopy (GC-MS).

Example 8: Catalytic Reduction of CO$_2$ to Methanol at Low Mass Flow Rates

CZA catalyst with a ratio of Cu:Zn of approximately 2.33 is loaded into a fixed bed flow reactor. The catalyst is reduced under 100 psi of flowing H$_2$ at 300° C. and 5,000 GHSV. The reactor is pressurized to 1,000 psi and a mixture of CO$_2$ and H$_2$ gas with a molar ratio of 1:3 is introduced at a GHSV of 1,000. Unreacted product gases are recycled through the reactor, while product liquids are condensed and extracted. The resulting product liquid is produced at a rate of approximately 0.1 kg/L$_{cat}$h and is comprised of approximately 64% methanol in water. Detectable byproducts include minimal quantities of ethanol, acetic acid, and n-propanol. Production at a low areal productivity due to low mass flow rates increased the per-pass conversion of CO$_2$ and H$_2$ to methanol, reduced the concentration of byproducts, and improved product purity.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method for reducing $CO_2$, comprising contacting a modified CZA catalyst with a feed mixture comprising $CO_2$ and a reductant gas at a reduction temperature and a reduction pressure, thereby providing a liquid product mixture, wherein the modified CZA catalyst comprises:

copper;

zinc;

one or more first elements being cobalt oxide, and optionally iron oxide;

aluminum;

oxygen; and optionally, one or more second elements selected from a Group V, VI, VII, VIII, IX, X, and XI metal, and wherein:

(A) the first element is present in an amount of about 1 to about 40 wt. % of the total amount of the copper, zinc, the first element, and the optional second element;

(B) wherein the molar ratio of copper to zinc is from about 2 to about 4.

2. The method of claim 1, wherein the reductant gas is $H_2$.

3. The method of claim 1, where the reductant gas is a hydrocarbon selected from $CH_4$, ethane, propane, or butane.

4. The method of claim 1, wherein the reductant gas is, or is derived from, flare gas, waste gas, or natural gas.

5. The method of claim 1, wherein the feed mixture comprises less than 25% of CO, less than 20% of CO, less than 15% of CO, less than 10% of CO, less than 5% of CO, or less than 1% of CO.

6. The method of claim 1, wherein the feed mixture is substantially free of CO.

7. The method of claim 1, wherein the method is selective for ethanol.

8. The method of claim 1, wherein the liquid product mixture comprises less than about 50 ppm formaldehyde.

9. The method of claim 1, wherein the catalyst comprises iron at a molar ratio of about 0.5 to about 1.5 relative to copper.

10. The method of claim 1, wherein the catalyst comprises one or more Group IA metals.

11. The method of claim 1, wherein the catalyst comprises cobalt oxide, iron oxide, copper, zinc oxide, and alumina.

12. The method of claim 1, wherein the catalyst comprises:

copper at a molar ratio of about 2.5 relative to the iron;

zinc oxide at a molar ratio of about 1 relative to the iron; and alumina at a molar ratio of about 0.35 relative to the iron.

*     *     *     *     *